United States Patent [19]

Pelzer et al.

[11] Patent Number: 5,254,672
[45] Date of Patent: Oct. 19, 1993

[54] SYNTHETIC PEPTIDES WHICH CONTAIN SEQUENCES FROM FACTOR VIIA, AND THE USE THEREOF

[75] Inventors: Hermann Pelzer, Marburg; Werner Stüber, Lahntal, both of Fed. Rep. of Germany

[73] Assignee: Behringwerke Aktiengesellschaft, Marburg, Fed. Rep. of Germany

[21] Appl. No.: 666,913

[22] Filed: Mar. 11, 1991

[30] Foreign Application Priority Data

Mar. 13, 1990 [DE] Fed. Rep. of Germany ....... 4007902

[51] Int. Cl.$^5$ .......................... C07K 7/00; C07K 17/00
[52] U.S. Cl. .................................. 530/328; 530/381; 530/402; 530/403; 530/806; 530/807; 530/810; 530/811; 530/812
[58] Field of Search ............... 530/381, 811, 812, 402, 530/403, 328; 435/69.1, 69.6; 514/15

[56] References Cited

U.S. PATENT DOCUMENTS 4,784,950 11/1988 Hagen et al. .......................... 435/68

OTHER PUBLICATIONS

Thim et al. (1988, Oct.) Biochemistry 27:7785-7793.
Takeya et al. (1988, Oct.) J. Biol. Chem. 263(29):14868-14877.
Freifelder (1976) Physical Biochemistry, Freeman & Co., San Francisco, pp. 236-237.
O'Hara et al. (1987) Proc. Natl. Acad. Sci. USA 84:5158-5162.
Murray et al. (1988) Nucler Acids Res. 16:4166
Hagen et al. (1986) Proc. Natl. Acad. Sci. USA 83:2412-2416.
Broze et al. (1980) J. Biol. Chem. 255(4):1242-1247.
Flengsrud (1979) Eur. J. Biochem. 98:455-464.
Bach et al. (1984) Blood 63(2): 393-398.
Radcliffe et al. (1976) J. Biol. Chem. 251(16):4797-4802.
Brandt et al., Am. J. Clin Pathol., 85, 583-589 (1986).
Boyer et al., Thrombosis and Haemostasis, 56, 250-255 (1986).
Nakane et al., The Journal of Histochemistry and Cytochemistry, 22, 1084-1091 (1974).
Axen et al., Nature, 214, 1302-1304 (1967).

Primary Examiner—Robert A. Wax
Assistant Examiner—Richard C. Ekstrom
Attorney, Agent, or Firm—Finnegan, Henderson, Farabow, Garrett & Dunner

[57] ABSTRACT

The invention relates to synthetic peptides which contain certain partial sequences from factor VIIa, the synthesis thereof and the use of these peptides for immunizing an animal and for purifying specific antibodies against the said peptides, to antibodies against these peptides and the use of these antibodies and peptides in therapy and diagnosis.

2 Claims, No Drawings

SYNTHETIC PEPTIDES WHICH CONTAIN SEQUENCES FROM FACTOR VIIA, AND THE USE THEREOF

The invention relates to synthetic peptides which contain certain partial sequences from factor VIIa, the synthesis thereof and the use of these peptides for immunizing an animal and for purifying specific antibodies against the said peptides, to antibodies against these peptides and the use of these antibodies and peptides in therapy and diagnosis.

The body is protected from the loss of blood by the clotting system. In the course of the clotting cascade a factor VII/tissue factor (TF) complex which is converted to the factor VIIa/TF complex by limited proteolysis, probably by traces of factor Xa, is formed here. The factor VIIa/TF complex has a proteolytic activity which is increased many-fold in comparison with free factor VIIa. The specific cleavage of the factor VII molecule takes place on the peptide bond following the tetrapeptide Pro-Gln-Gly-Arg. This cleavage results in a two-chain factor VIIa molecule consisting of a light chain of 152 amino acids and a heavy chain of 254 amino acids. The two chains are held together by a disulfide linkage. On activation, i.e. cleavage, of the one-chain factor VII molecule resulting in the two-chain factor VIIa molecule, a new carboxy terminal or amino terminal amino acid sequence is generated on the light or heavy chain of the factor VIIa molecule. With the aid of a specific antibody which exclusively recognizes the carboxy terminal or amino terminal amino acid sequence newly formed after factor VIIa formation, but does not recognize the native factor VII, a specific determination of factor VIIa in blood or plasma can be carried out. Thereby allowing the quantification of the clotting capacity generated in the initial phase of the extrinsic coagulation pathway.

The determination of the functional activity of factor VII using factor VII-deficient plasma is known (John T. Brandt et al., Am.J.Clin.Patrol. 85 (1986), 583–589). In this procedure the effect of diluted plasma in shortening the clotting time is determined in a system which contains all the factors necessary for the clotting process with the exception of factor VII. The test determines the complete proportion of factor VII which can be activated in the plasma sample, but is not capable of quantifying the concentration of active factor VII a already present.

A process for the quantification (C. Bayer et al., Thrombosis and Haemostasis, 56 (3) (1986), 250–255) of factor VII using radioimmunoassays or enzyme immunoassays is also known. The antibodies necessary for this procedure are generated by using factor VII purified from plasma to immunize animals The antibodies obtained are suitable for the quantitive determination of factor VII, but do not discriminate between inactive factor VII and active factor VIIa.

The present invention was therefore based on the object of providing antigens inducing specific antibodies against factor VIIa. A further object was to develop a test method using specific factor VIIa antibodies, which method allows a sensitive and accurate quantification of factor VIIa or factor VIIa/TF complex in biological fluids.

This object is achieved according to the invention by synthetic peptides which contain amino acid sequences which are in part identical to the amino acid sequence of factor VIIa and are antigenic.

The invention therefore relates to peptides which contain amino acid sequences which are in part identical to the carboxy terminus or amino terminus of factor VIIa resulting from the factor Xa cleavage of factor VII, which sequences contain the amino acid sequence H-Ser-Asp-His-Thr-Gly-Thr-Lys-Arg-Ser-Cys-Arg-Cys-His-Glu-Gly-Tyr-Ser-Leu-Leu-Ala-Asp-Gly-Val-Ser-Cys-Thr-Pro-Thr-Val-Glu-Tyr-Pro-Cys-Gly-Lys-Ile-Pro-Ile-Leu-Glu-Lys-Arg-Asn-Ala-Ser-Lys-Pro-Gln-Gly-Arg-OH and/or the sequence H-Ile-Val-Gly-Gly-Lys-Val-Cys-Pro-Lys-Gly-Glu-Cys-Pro-Trp-Gln-Val-Leu-Leu-Leu-Val-Asn-Gly-Ala-Gln-Leu-Cys-Gly-Gly-Thr-Leu-Ile-Aln-Thr-Ile-Trp-Val-Val-Ser-Ala-Ala-His-Cys-Phe-Asp-Lys-Ile-Lys-Asn-Trp-Arg-OH entirely or in part, but at least the four carboxy terminal and/or amino terminal amino acids (Pro-Gln-Gly-Arg-OH and/or H-Ile-Val-Gly-Gly).

The invention furthermore relates to the use of the peptides according to the invention for obtaining antibodies, where the antibodies are preferably obtained by immunoadsorptive purification from polyclonal antisera.

The invention also relates to the use of the antibodies according to the invention and/or the peptides according to the invention for determining factor VIIa or factor VIIa/TF complex.

The invention also relates to the use of the peptides according to the invention and of the antibodies against them for therapeutic purposes, in particular for the therapy of disorders of the clotting system. The peptides according to the invention can be prepared by processes known per se to those skilled in the art and e.g. protected amino acid derivatives or peptide segments can, in this connection, be coupled to one another in solution or on a solid phase and peptides according to the invention can be obtained by cleaving off the protecting groups and, in the case of a solid phase, by cleaving off the carrier resin.

As temporary protecting group, the Fmoc group, the permanent protecting groups for the side chain functionalities based on t-butyl/Boc, the Pmc or Mtr group for Arg and the tert.-butylmercapto groups or trityl groups for Cys are preferably used in this connection. The C-terminal amino acid is immobilized via p-alkoxybenzylester groups which are linked to a polymeric carrier, preferably crosslinked polystyrene, which is normally suitable for peptide synthesis. The peptide synthesis is carried out by repetitively cleaving off Fmoc, preferably using 20% piperidine in DMF (dimethylformamide) (V/V), and coupling the subsequent protected amino acid, preferably using a carbodiimide in the presence of HOBT. The amino acid derivative is, for this purpose, coupled using a preferably 3-fold excess in the course of 1–1.5 hours in DMF. After each step, cleaving off of Fmoc or condensation step, the resin is washed 3 times in each case with small (15 ml/g) portions of DMF and isopropanol. The peptides according to the invention are cleaved off acidolytically with simultaneous liberation of the side chain functionalities. Sulfhydryl groups which may have to be rendered free are "deprotected" using tri-n-butylphosphine in an alcohol, for example trifluoroethanol, or using DTT in water. In the case of the Cys (Trt) deprotection, a separate step is unnecessary when using ethanedithiol as scavenger. The purification of the peptides can e.g. be carried out by ion exchange chromatography, reversed-phase chromatography and gel permeation chromatography. The correct composition of the peptides and the peptide contents are determined by amino acid analysis.

The use of synthetic peptides as antigens in the immunization of animals results in the generation of antibodies specifically directed against the hapten exposed in this peptide. The antibodies generated in this way are therefore specific for in each case a single antibody binding site of the entire protein from which the peptide sequence has been derived The use of synthetic peptides has substantial advantages in comparison with the use of conventionally purified factor VIIa; it is possible to prepare synthetic peptides on a large scale and in high purity so that a complicated isolation and purification of natural factor VIIa is not necessary. While the purification of synthetic peptides from by-products of the synthesis is well established, even technically sophisticated concentration and purification processes for natural factor VIIa always lead to preparations which contain a very small, but antigenically active proportion of undesired peptides, for example native factor VII. Moreover, when using complete factor VII or factor VIIa as immunization antigen a multitude of antibody populations which, in the end, are directed against all the haptens exposed in these proteins are always obtained; because of this multitude of different antibodies it is difficult to find specific antibodies which are directed exclusively against factor VIIa.

It has now been found that antibodies which are directed against a peptide or polypeptide which contains at its C-or N-terminal end the recognition sequence for factor Xa react exclusively with factor VIIa in a specific way, but not with the intact uncleaved factor VII. The 2 chains resulting from the action of factor Xa on factor VII, which C- or N-terminally contain the factor Xa recognition sequence, consist of 152 and 254 amino acids, respectively. For the immunization, both the complete polypeptides and partial sequences of these peptides which, however, must still contain the factor Xa recognition sequence at the C- or N-terminus are suitable. A particularly preferred embodiment provides the use of decapeptides, for example containing the sequences Cys-Arg-Asn-Ala-Ser-Lys-Pro-Gln-Gly-Arg or Ile-Val-Gly-Gly-Lys-Val-Cys-Pro-Lys-Gly.

It is important for the case mentioned that the carboxy terminal or amino terminal sequence of the molecule is exposed and leads to immunization.

In view of the potential use of the peptides it is useful to introduce into the peptides amino acids containing reactive side groups, in such a way that they do not impair the structure of the hapten. For this reason, cysteine whose free SH group is suitable for coupling via thioether to many carriers is, if appropriate, advantageously attached N- or C-terminally. Preferably, e.g. the antigen represented by the abovementioned peptide is provided in the form of the decapeptide Cys-Arg-Asn-Ala-Ser-Lys-Pro-Gln-Gly-Arg.

The preparation of the peptide used for the immunization can be prepared both by chemical synthesis in a manner known to those skilled in the art and by purification of a polypeptide provided by genetic engineering.

Peptides which are intended to be used for immunization or those which are intended to be used as immunoadsorbent are, to be useful, coupled to a carrier molecule. Coupling methods are known per se to those skilled in the art and are described in the literature (Nakane, P.K. et al., J. Histochem. Cytochem. 22 (1974), 1084-1091). Carrier molecules for the purpose of this invention may be natural or synthetic macromolecules such as those used by those skilled in the art for preparing an immunoreactive conjugate, such as e.g. albumin, ovalbumin, keyhole limpet hemocyanin or polysaccharides. In a preferred embodiment the peptide or polypeptide is coupled to the hemocyanin of a marine limpet, the keyhole limpet hemocyanin.

When using the synthetic peptides according to the invention as immunoadsorbent, it is advisable to couple to materials which are suitable for providing solid matrices. Carriers for this purpose are insoluble polymers such as those used by those skilled in the art for immobilizing proteins and peptides, such as e.g. polystyrene, nylon, agarose or magnetizable particles. The solid phase can here be present in any desired form, e.g. as tube, fabric, bead or microparticle.

A preferred embodiment provides for the coupling of peptides, e.g. of the abovementioned decapeptides, to cyanogen bromide-activated Sepharose.

The immunization of suitable animals with carrier-bound peptides reproducibly results in the formation of antibodies. A preferred animal species for immunization and obtaining antibodies is the rabbit in this case; additionally mice can also be used for the immunization.

From such an antiserum which has been generated according to the invention in an animal using synthetic peptides, the immunoglobulin fraction relevant for specific tests can be enriched by conventional immunoadsorptive methods. However, it is preferred in this case to use a peptide which is also coupled to a carrier and has the same antigenic determinant as the peptide used in the immunization as material for such a matrix employed for the immunoadsorption. The peptide used for the immunoadsorptive purification can also contain a shortened amino acid sequence; the precondition for use in the immunoadsorptive purification of the desired antibody is merely that the antigenic determinant of this shortened polypeptide sequence is recognized by the desired antibody and is bound effectively.

The peptide used for the immunoadsorptive isolation of the antibodies can e.g. be a decapeptide, preferably the peptide Cys-Arg-Asn-Ala-Ser-Lys-Pro-Gln-Gly-Arg. According to the invention antibodies are induced in an animal system by immunizing with synthetic peptides and are purified by immunoadsorption. These antibodies specifically react with the peptides used for the immunization and purification Depending on the sequence of the peptide used, these antibodies bind either only to factor VIIa or, if a peptide sequence exposed in the native factor VII molecule is chosen, also to the intact factor VII molecule.

By selecting appropriate peptides as immunosorbents, it is possible to select antibodies which specifically react with the antigenic determinants of the factor VIIa, which correspond to the recognition sequence of the factor Xa cleavage site of this molecule. In the case where peptides which have a C- or N-terminal factor Xa recognition sequence are used both for the immunization and for the immunoadsorptive purification, which is preferred, antibodies against these sequences are enriched. However, these do not react with intact native factor VII, since, in the intact factor VII molecule, the factor Xa cleavage site either is not exposed fully enough or does not have the higher structure necessary for antigenic recognition.

Using methods known per se to those skilled in the art, monoclonal antibodies having the properties according to the invention can also be prepared.

The antibodies obtained according to the invention can be employed in homogeneous and heterogeneous immunoassays, which are known per se to those skilled in the art, such as e.g. enzyme immunoassays, or free or latex-enhanced agglutination reactions. They are preferably coupled to a solid carrier for this purpose. Such solid carriers are known per se to those skilled in the art, such as e.g. microtitration plates, tubes, beads, microbeads, magnetizable particles and the like. In this connection the immobilization on polystyrene tubes or microtitration plates is preferred. The tubes which have been prepared for the immunoassays which follow can then be stored, sealed air-tight, e.g. at 4° C.

The factor VIIa content is determined according to the invention by preincubation of the sample with immobilized antibodies of this type, the concentration of the factor VIIa bound by the immobilized antibodies being detected by a subsequent incubation with a second antibody. This second antibody has to have a property which can be measured, e.g. the capability to convert or bind a chromogenic substrate.

The second antibody can e.g. be provided with an enzyme, a fluorescent molecule, such as e.g. fluorescein isothiocyanate, a radioactive label or a molecule capable of chemoluminescence. Preferably, this second antibody is coupled to a marker enzyme, peroxidase being particularly preferred.

According to the invention, the concentration of factor VIIa/TF complex can also be determined with an antibody immobilized in this way. As a precondition, a specific antibody against tissue factor must be used as second antibody which is labeled in the way described. TF antibodies can be obtained by methods known per se to those skilled in the art as polyclonal or monoclonal antibodies. It is also possible for the TF antibody to be bound and the factor VIIa antibody to be labeled.

Factor VIIa or factor VIIa/TF complex can also be determined by simultaneous incubation of the sample, preferably of plasma and labeled antibody, with the immobilized antibodies. In addition to this a competitive determination method is possible, where labeled and unlabeled factor VIIa or factor VIIa/TF complex compete for the binding site of the immobilized antibodies. The factor VIIa content determined in this way allows a statement on the degree of activation of the factor VII. The embodiments described in the examples are particularly preferred.

The examples illustrate the invention but do not restrict it in any way.

The following abbreviations are used in the examples:

| | |
|---|---|
| ELISA | enzyme immunoassay (enzyme linked immunosorbent assay) |
| KLH | keyhole limpet hemocyanin (hemocyanin of a marine limpet) |
| PBS | phosphate-buffered saline |
| Tris | tris(hydroxymethyl)aminomethane |
| OD | extinction (optical density) |
| Cys, C | cysteine   amino acids can be in the D- or |
| Ala, A | alanine    L form, but are, if not stated |
| Arg, R | arginine   specially, in the L form. |
| Pro, P | proline |
| Phe, F | phenylalanine |
| Lys, K | lysine |
| Ile, I | isoleucine |
| Gly, G | glycine |
| Glu, E | glutamic acid |
| Thr, T | threonine |
| Gln, Q | glutamine |
| Boc | t-butoxycarb-onyl |
| Fmoc | 9-fluorenylmethoxycarbonyl |
| Mtr | 4-methoxy-2,3,6-trimethylphenylsulfonyl |
| DMF | dimethylformamide |
| HoBt | hydroxybenzotriazole |
| DTT | dithiothreitol |
| Trt | trityl |
| Pmc | 2,2,5,7,8-pentamethylchroman-6-sulfonyl |

EXAMPLE 1

Preparation of an Antigen for Immunization a) Synthesis of Cys-Arg-Asn-Ala-Ser-Lys-Pro-Gln-Gly-Arg 1. g of Fmoc-Arg (Pmc)-p-alkoxybenzyl ester-resin was washed 2×with 15 ml of DMF for 1 min and the Fmoc group was cleaved off using 15 ml of 20% piperidine/DMF (V/V) (1×3 min, 1×10 min). The resin was subsequently washed 3×in each case with DMF and isopropanol (15 ml in each case) and 2×with 15 ml of DMF. 1.5 mmol of Fmoc-amino acid and 2.25 mmol of HOBt dissolved in 15 ml of DMF were added to the resin and, after adding 1.65 ml of a 1M diisopropylcarbodiimide solution in dichloromethane, the mixture was agitated at room temperature for 1.5 h. Using a ninhydrin test, it was tested whether the reaction was complete Then the resin was washed with 3×in each case with DMF or isopropanol (15 ml in each case) and a new cycle was started. A Boc-Cys (Trt) was used in the last cycle. The resin was washed 3×with 15 ml in each case of isopropanol and diethyl ether and dried in high vacuum. 1.9 g of resin was stirred with 1 ml of thioanisole, 1 ml of ethanedithiol and 18 ml of trifluoroacetic acid at room temperature for 2 h, filtered off, the resin was washed with 3 portions of trifluoroacetic acid/dichloromethane (1:1) and the filtrates were crystallized in ether. The crude peptide was washed with diethyl ether and dried. The peptide was chromatographed on ®Sephadex G 25 in 0.5% acetic acid. Yield: 649 mg.

100 mg of this product were chromatographed on a preparative HPLC apparatus on reversed-phase material for further purification (0.1% acetonitrile, gradient mode). The peptide pool was freeze-dried. Yield: 48 mg.

b) Conjugate Preparation 20 mg of KLH were dissolved in 0.05 mM sodium phosphate buffer, pH 8.0, and stirred with 2 mg of hydroxysuccinimide ester of gamma-maleimidobutyric acid for 1 h. The protein was chromatographed on a ®Sephadex G 50 column (2×30 cm) (0.1M sodium phosphate, 0.5 mM EDTA, pH 6.0). The eluate was concentrated to 5 ml and incubated with 20 mg of peptide for 1 h. After dialysis and freeze-drying, 28 mg of peptide conjugate were obtained.

EXAMPLE 2

Immunization of Rabbits 5 rabbits were immunized with 2 mg of antigen in each case per animal over a period of 8 weeks; the peptide-KLH conjugate was administered subcutaneously and intravenously. The animals were then bled, and the crude antisera obtained were pooled and stabilized with a preservative. Yield: 175 ml of antiserum per animal.

EXAMPLE 3

Preparation of Immunoadsorbents

For the purification of the crude antisera by affinity chromatography, about 30 mg of decapeptide of the sequence Cys-Arg-Asn-Ala-Ser-Lys-Pro-Gln-Gly-Arg (prepared as in Example 1a) were immobilized covalently on a solid phase. The coupling reaction was carried out using cyanogen bromide-activated Sepharose according to a process which had been described (Axen, R. et al., Nature, 214, 1302, 1967). The immunoadsorbent was then in each case washed with phosphate-buffered saline (PBS; 0.15 mol/l, pH 7.2) and acetic acid (0.5 ml/l, pH 2.5). Before use, the adsorbent was equilibrated with 3 times the volume of the gel in PBS. Yield: about 30 ml of peptide-Sepharose.

EXAMPLE 4

Isolation of Specific Antibodies 100 ml of crude antiserum were applied to the 30 ml of peptide-Sepharose (1.6×15 cm) equilibrated with PBS, and then washed with PBS until the extinction at 280 nm was 0.01. Washing steps using saline (1 mol/l, pH 7.0) and water (pH 7.0) were then carried out, 3 times the volume of the gel being used in each case. The antibodies were eluted from the immunoadsorbent using acetic acid (0.1 mol/l, pH 2.5), and the antibody solution was adjusted to pH 7.0 using solid sodium phosphate (0.01 mol/l), concentrated (Amicon membrane) and stored at −70° C. Yield: about 35 mg of antibody.

EXAMPLE 5

Testing of Antibodies Obtained by Immunoadsorption a) Preparation of Antibody-Coated Tubes

The antibodies obtained in Example 4 were diluted to a concentration of 5 µg/ml using Tris buffer solution (0.025 mol/l, pH 7.6) and immobilized by adsorption to polystyrene tubes. Per tube, 250 µl of antibody solution was incubated at 20° C. for 20 hours, the liquid was then aspirated and the tubes were stored, sealed air-tight, at 4° C.

b) Procedure for the Enzyme Immunoassay (ELISHA)

The samples to be tested were diluted 1+1 using incubation buffer (50 mM Tris, 100 mM NaCl, 0.1% azide, pH 7.2) and 200 µl in each case per tube (see Example 5a) were incubated at 37° C. for 30 min. The incubation solution was then removed and the tube was washed twice with 500 µl of washing solution (0.02 mol/l sodium phosphate, 0.5% Tween, pH 7.6) in each case, Subsequently, 200 µl of peroxidase-conjugated anti-tissue factor antibody were added and the tubes were incubated at 37° C. for 30 min. After removing the conjugate solution and washing twice, 200 µl of substrate/chromogen solution (hydrogen peroxide; o-phenylenediamine) were added and the tubes were incubated at room temperature. After incubation for half an hour, the peroxidase was inactivated using sulfuric acid and the extinction of the reaction solution was determined at 492 nm.

c) Determination of Factor VIIa/TF Complex Formed in vitro by means of Enzyme Immunoassay In an in vitro experiment, a thromboplastin solution was added to plasma and incubated at 37° C. for 150 min. The sample was then diluted 1+9 with PBS and the formed factor VIIa/TF concentration was determined in an ELISA. In the table below the extinction values (492 nm) of a plasma sample at the moment of thromboplastin addition and 150 min after the addition are shown; the extinction of a tube without plasma is used as comparison.

TABLE 1

| Sample | $OD_{492}$/30 min |
|---|---|
| Plasma + thromboplastin (0 min of incubation) | 0.34 |
| Plasma + thromboplastin (150 min of incubation) | 0.82 |
| Buffer blank | 0.16 |

In a further experiment the specificity of the antibodies against factor VIIa was tested. Thromboplastin solution was added to plasma anticoagulated with citrate solution and the mixture was incubated at 37° C. At various times aliquots were taken and the reaction was stopped by addition of citrate (final concentration: 0.15 mol/l). The samples were diluted 1+1 using incubation buffer and tested using the ELISA.

The table shows the results:

TABLE 2

| Time (min) | $OD_{492}$/30 min |
|---|---|
| 0 | 0.25 |
| 5 | 0.39 |
| 10 | 0.53 |
| 20 | 0.60 |
| 60 | 0.71 |
| 75 | 0.79 |
| Plasma blank | 0.24 |

The results indicate that the factor VIIa/TF complex can be quantitatively measured in this way: during the activation reaction the concentration of factor VIIa/TF complex increases with time.

The peptides according to the invention, which contain an amino acid sequence which is completely or partly identical to the amino acid sequence of factor VII and is antigenic, thus induce the binding-specific antibodies against the particular antigenic determinants present in the peptide. These specific antibodies can then be purified by immunoadsorption on peptides containing the same antigenic determinant. The use of synthetic peptides has the substantial advantage that absolutely pure antigens are used for the immunization so that no cross reactivity whatsoever with other proteins or other parts of the factor VII molecule can occur in the resulting antiserum. According to the invention a peptide which corresponds to the C- or N-terminal amino acid sequence of the factor Xa cleavage site in the factor VII molecule is preferably used. Using an antibody against this peptide it is possible to detect selectively cleaved factor VII molecules, i.e. factor VIIa, since this antibody recognition sequence is not accessible in the intact native factor VII. The determination of the amount of bound antibody by means of ELISA allows the direct quantitation of factor VIIa or factor VIIa/TF complex formed and therefore to make a statement on the degree of activation of factor VII.

We claim:

1. Synthetic decapeptide selected from the group consisting of:

Cys-Arg-Asn-Ala-Ser-Lys-Pro-Gln-Gly-Arg and

Ile-Val-Gly-Gly-Lys-Val-Cys-Pro-Lys-Gly, said peptide being chemically synthesized and being antigenic.

2. The peptide of claim 1 coupled to a carrier molecule directly or via a spacer.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 50
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( i x ) FEATURE:
        ( D ) OTHER INFORMATION: listed in text as
    H- Ser-Asp-His-Thr-Gly-Thr-Lys-Arg-Ser-Cys-Arg-Cys-His-Glu-Gly-Tyr
    - Ser-Leu-Leu-Ala-Asp-Gly-Val-Ser-Cys-Thr-Pro-Thr-Val-Glu-Tyr-Pro-
    Cys- Gly-Lys-Ile--Pro-Ile-Leu-Glu-Lys-Arg-Asn-Ala-Ser-Lys-Pro-Gln-
    Gly- Arg-OH ( x i ) SEQUENCE DESCRIPTION: SEQ ID NO: 1:

```
Ser  Asp  His  Thr  Gly  Thr  Lys  Arg  Ser  Cys  Arg  Cys  His  Glu  Gly  Tyr
 1              5                        10                       15

Ser  Leu  Leu  Ala  Asp  Gly  Val  Ser  Cys  Thr  Pro  Thr  Val  Glu  Tyr  Pro
               20                       25                       30

Cys  Gly  Lys  Ile  Pro  Ile  Leu  Glu  Lys  Arg  Asn  Ala  Ser  Lys  Pro  Gln
               35                       40                       45

Gly  Arg
 50
```

( 2 ) INFORMATION FOR SEQ ID NO: 2:

( i ) SEQUENCE CHARACTERISTICS:
        ( A ) LENGTH: 50
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( i x ) FEATURE:
        ( D ) OTHER INFORMATION: listed in text as H-Ile-Val-Gly-Gly-
    Lys-Val-Cys-Pro-Lys-Gly-Glu-Cys-Pro-Trp-Gln-Val-Leu-Leu-Leu-Val-
    Asn-Gly-Ala-Gln-Leu-Cys-Gly-Gly-Thr-Leu-Ile-Asn-Thr-Ile-Trp-Val-
    Val-Ser-Ala-Ala-His-Cys-Phe-Asp-Lys-Ile-Lys-Asn-Trp-Arg-OH ( x i ) SEQUENCE DESCRIPTION: SEQ ID NO: 2:

```
Ile  Val  Gly  Gly  Lys  Val  Cys  Pro  Lys  Gly  Glu  Cys  Pro  Trp  Gln
 1              5                        10                       15

Val  Leu  Leu  Leu  Val  Asn  Gly  Ala  Gln  Leu  Cys  Gly  Gly  Thr  Leu
               20                       25                       30

Ile  Asn  Thr  Ile  Trp  Val  Val  Ser  Ala  Ala  His  Cys  Phe  Asp  Lys
               35                       40                       45

Ile  Lys  Asn  Trp  Arg
                50
```

( 2 ) INFORMATION FOR SEQ ID NO: 3:

( i ) SEQUENCE CHARACTERISTICS:
        ( A ) LENGTH: 4
        ( B ) TYPE: amino acid
        ( C ) STRANDEDNESS:
        ( D ) TOPOLOGY: linear ( i i ) MOLECULE TYPE:

(A) DESCRIPTION: peptide (ix) FEATURE:
(D) OTHER INFORMATION: hydroxylated (xi) SEQUENCE DESCRIPTION: SEQ ID NO: 3:

Pro Gln Gly Arg
1

(2) INFORMATION FOR SEQ ID NO: 4:

(i) SEQUENCE CHARACTERISTICS:
(A) LENGTH: 4
(B) TYPE: amino acid
(C) STRANDEDNESS:
(D) TOPOLOGY: linear (ii) MOLECULE TYPE:
(A) DESCRIPTION: peptide (ix) FEATURE:
(D) OTHER INFORMATION: hydrogenated (xi) SEQUENCE DESCRIPTION: SEQ ID NO: 4:

Ile Val Gly Gly
1

(2) INFORMATION FOR SEQ ID NO: 5:

(i) SEQUENCE CHARACTERISTICS:
(A) LENGTH: 10
(B) TYPE: amino acid
(C) STRANDEDNESS:
(D) TOPOLOGY: linear (ii) MOLECULE TYPE:
(A) DESCRIPTION: peptide (ix) FEATURE:
(D) OTHER INFORMATION:

(xi) SEQUENCE DESCRIPTION: SEQ ID NO: 5:

Cys Arg Asn Ala Ser Lys Pro Gln Gly Arg
1               5                   10

(2) INFORMATION FOR SEQ ID NO: 6:

(i) SEQUENCE CHARACTERISTICS:
(A) LENGTH: 10
(B) TYPE: amino acid
(C) STRANDEDNESS:
(D) TOPOLOGY: linear (ii) MOLECULE TYPE:
(A) DESCRIPTION: peptide (ix) FEATURE:
(D) OTHER INFORMATION:

(xi) SEQUENCE DESCRIPTION: SEQ ID NO: 6:

Ile Val Gly Gly Lys Val Cys Pro Lys Gly
1               5                   10